United States Patent [19]

Bruso

[11] Patent Number: 4,636,472
[45] Date of Patent: Jan. 13, 1987

[54] DISPOSABLE STERILIZATION BIOLOGICAL TEST PACK

[75] Inventor: Loran H. Bruso, Ontario, Calif.

[73] Assignee: Warner-Lambert Company, Morris Plains, N.J.

[21] Appl. No.: 735,226

[22] Filed: May 16, 1985

[51] Int. Cl.⁴ .............................................. C12M 1/34
[52] U.S. Cl. .................................... 435/287; 435/31; 435/810
[58] Field of Search ................. 435/31, 287, 296, 810; 422/58

[56] References Cited

U.S. PATENT DOCUMENTS

| | | | |
|---|---|---|---|
| 3,239,429 | 3/1966 | Menolasino et al. | 195/54 |
| 3,440,144 | 4/1969 | Andersen | 195/103.5 |
| 3,661,717 | 5/1972 | Nelson | 195/103.5 R |
| 3,996,802 | 12/1976 | Smith | 73/356 |
| 4,291,122 | 9/1981 | Orelski | 435/31 |
| 4,304,869 | 12/1981 | Dyke | 435/296 |
| 4,397,945 | 8/1983 | Lemonnier | 435/31 |
| 4,486,387 | 12/1984 | Augurt | 422/58 |

*Primary Examiner*—Alan Cohan
*Attorney, Agent, or Firm*—Neil K. Nydegger

[57] ABSTRACT

A disposable sterilization test pack for determining the efficacy of sterilizing equipment comprises a porous base pad having a cavity for receiving the sterilization indicator. Porous pads are disposed on opposite sides of the base pad to retain the sterilization indicator within the cavity, and an impermeable layer is disposed against one of the porous pads to confine the introduction and evacuation of air from the test pack to the edges of the test pack and the exposed porous pad which is not covered by the impermeable layer.

20 Claims, 8 Drawing Figures

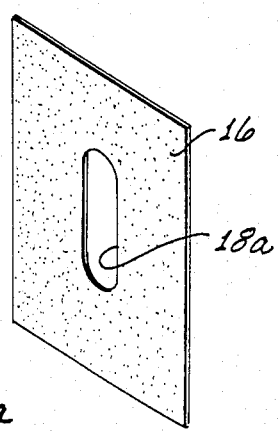
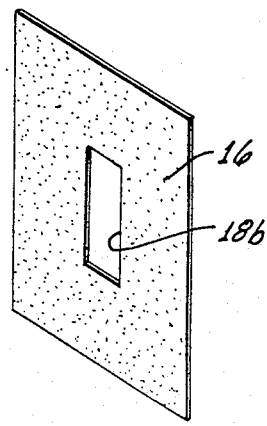
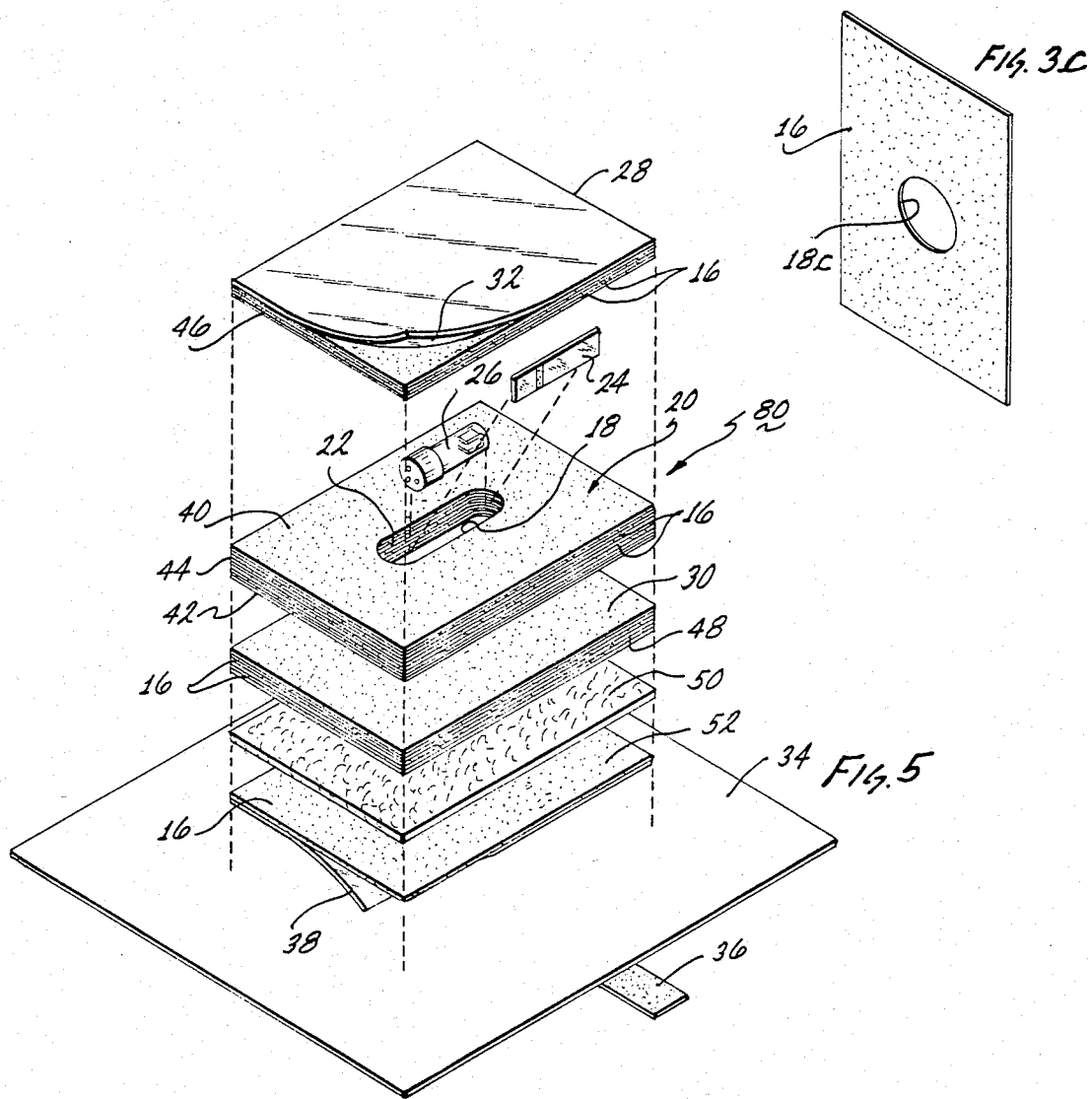

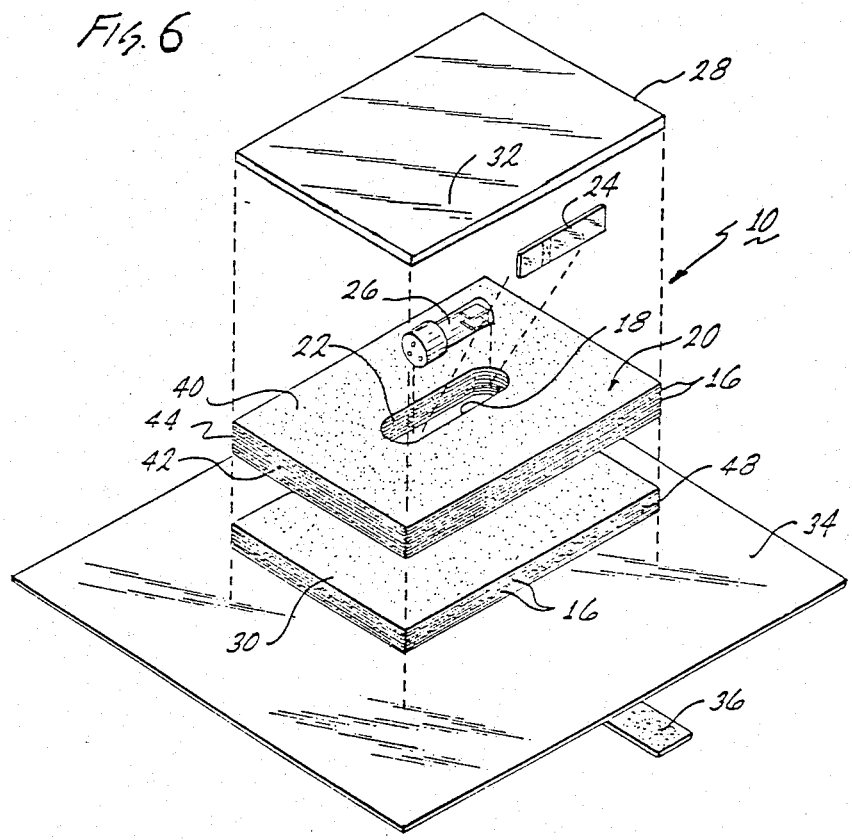

DISPOSABLE STERILIZATION BIOLOGICAL TEST PACK

BACKGROUND OF THE INVENTION

This invention relates generally to packs for testing the efficacy of a sterilization system. More specifically, the invention relates to a disposable test pack which can be used with either a biological indicator or a chemical indicator to determine the efficacy of the sterilization system. The present invention is particularly, though not exclusively, useful for the testing of sterilizing equipment used for the sterilization of hospital and medical equipment.

DESCRIPTION OF THE PRIOR ART

The sterilization of medical equipment by exposure to steam is typically accomplished by using an autoclave. Normally, the equipment to be sterilized is placed within the autoclave and a vacuum may be drawn depending on the particular procedure being followed. The sterilization medium, steam, is then introduced into the autoclave to permeate the equipment and sterilize it.

According to standard hospital procedures, steam sterilization equipment needs to be periodically tested to insure the sterilization process is efficacious. Such a test necessarily requires subjecting spores of living microorganisms to the sterilization cycle and subsequently observing whether they have remained viable. To insure that the sterilization process is efficacious by sufficiently challenging the sterilization equipment, these spores need to be protected as well or better than they would ordinarily be protected if lodged in the most inaccessible recesses of the hospital equipment to be sterilized.

Several procedures have been proposed to test the efficacy of steam sterilization equipment. Typical of these, and perhaps the best known and most widely used, is the procedure recently published by the Association for the Advancement of Medical Instrumentation (A.A.M.I.). According to the A.A.M.I. recommended practice, freshly laundered all-cotton towels are folded by hospital personnel and stacked to construct a test pack into which a biological indicator is imbedded. This pack is then subjected to the sterilization cycle.

Although apparently efficacious for its intended purpose, the construction of a test pack according to the A.A.M.I. procedure is labor intensive and the resulting pack is relatively bulky. In light of these limitations, the present invention satisfies the need for a pre-assembled composite sterilization test pack which is convenient to handle and which will sufficiently challenge steam sterilization equipment. This is accomplished by surrounding a biological indicator with material which will delay steam entry to the indicator and provide the indicator with a degree of thermal insulation.

Accordingly, it is an object of the present invention to provide a pre-assembled sterilization test pack which tests the efficacy of steam sterilization equipment by challenging the accessibility of steam to the indicator and providing a requisite level of thermal insulation for the indicator. It is yet another object of the present invention to provide a test pack which can be easily altered to change sterilization indicators according to the needs and desires of the operation. Still another object of the present invention is to provide a biological test pack which is small, compact and easily handled by hospital personnel. Another object of the invention is to provide a test pack which is convenient to use, standardized, cost effective and easily manufactured.

SUMMARY OF THE INVENTION

A preferred embodiment of the novel disposable sterilization test pack includes a base pad comprising a plurality of porous sheets having holes cut therethrough which are stacked to align the holes and form a cavity for receiving a sterilization indicator therein. A top pad and a bottom pad of gas permeable porous material are respectively placed against the top and bottom surfaces of the base pad to confine the indicator within the cavity and help inhibit the flow of gas to and from the cavity. A gas impermeable layer is disposed against the top pad on its surface which is opposite from the base pad to further inhibit gas flow to and from the cavity by preventing the passage of gas into and out of the test pack wherever the impermeable layer is in contact with the porous material of the top pad.

When subjected to a sterilization cycle, the sterilization indicator, positioned in the cavity of the test pack's base pad will react according to the efficacy of the sterilization cycle. As envisioned by the present invention, a biological and a chemical indicator can be used in the test pack for increased versatility and compatibility with the particular equipment being tested. The entire pack can be covered with a CSR (central supply room) overwrap material and held together with a tape having an indicator ink imprinted thereon to show when a pack has been subjected to a sterilization process.

The novel features of this invention, as well as the invention itself, both as to its structure and its operation, will be best understood from the accompanying drawings taken in conjunction with the accompanying description in which similar reference characters refer to similar parts and in which:

BRIEF DESCRIPTION OF THE DRAWINGS

FIG. 3a, b and c are perspective views of porous sheets used in the present invention showing various holes cut therethrough that can form cavity configurations in which sterilization indicators can be placed;

FIG. 5 is an exploded perspective view of the contents of an alternate embodiment of the sterilization test pack; and FIG. 6 is an exploded perspective view of the contents of another embodiment of the sterilization test pack.

DESCRIPTION OF THE PREFERRED EMBODIMENT

Figure 1:
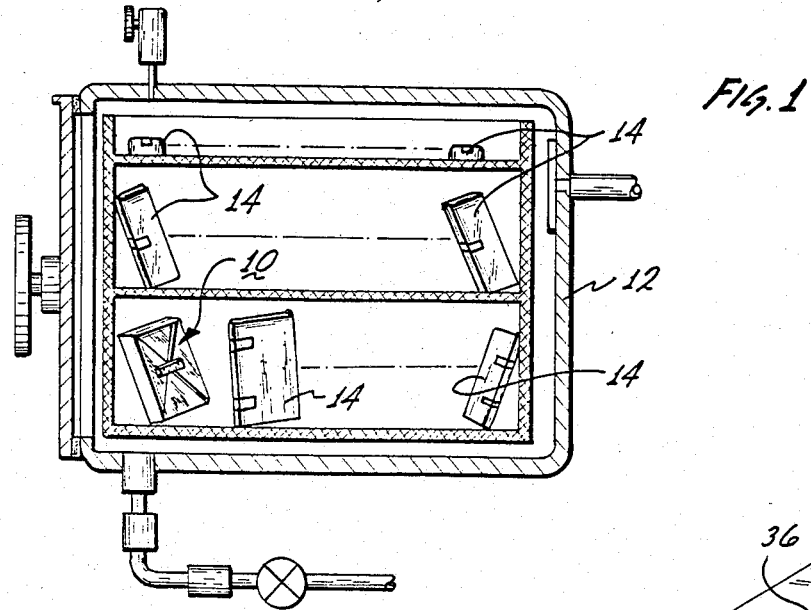
FIG. 1 is a side cross-sectional view of sterilization equipment showing the test pack of the present invention located therein.

FIG. 1 shows the test pack 10 of the present invention as it would be placed inside sterilization equipment 12 for testing the efficacy of the equipment 12. Also shown placed in equipment 12 are various bundles 14 of medical equipment which require sterilization.

Figure 2:
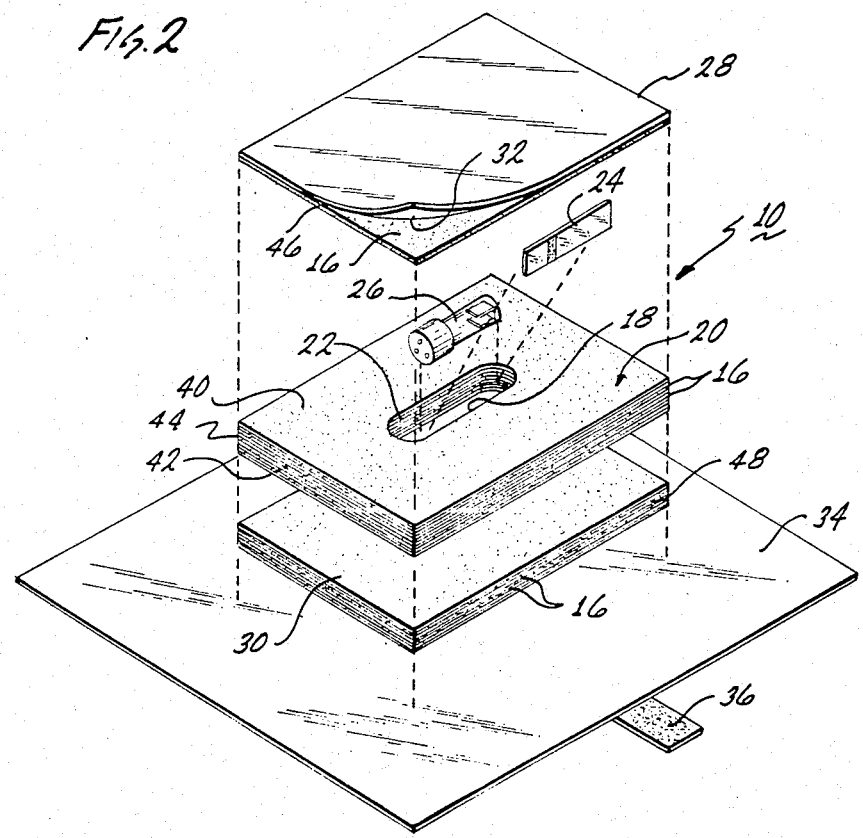
FIG. 2 is an exploded perspective view of the present invention.

Referring now to FIG. 2, it can be seen that test pack 10 comprises a base pad 20, a top pad 28 and a bottom pad 30 generally oriented with respect to each other as shown. With specific regard to base pad 20 and referece to FIG. 2, it will be appreciated that base pad 20 is constructed by stacking together several gas permeable porous sheets 16. As seen in FIGS. 3a, b and c, these sheets 16 can have several die cut configurations of which the variety of holes 18a, b and c shown respectively in FIGS. 3a, b and c are only exemplary. Several sheets 16, each having similar hole 18 configurations, are stacked together to form pad 20 with a cavity 22. It will be appreciated by the skilled artisan that, depending on the hole 18 configuration, cavity 22 can be formed in various shapes depending upon the needs and desires of the operator and according to the size, shape and configuration of the particular biological test indicator being used. In the preferred embodiment, the sheet 16 comprises a nonwoven gas permeable porous material such as heavy weight index paper which is well known in the pertinent art.

As seen in FIG. 2, base pad 20 is generally box-shaped and has a top surface 40, a bottom surface 42 and an edge 44 defined therebetween. As was the case with cavity 22, the particular shape of base pad 20 can be modified depending on the desires of the operator. However, as will be more clearly appreciated in subsequent discussion, the top surface 40 and the bottom surface 42 are preferably flat in order to engage with top pad 28 and bottom pad 30 in a manner to be subsequently discussed.

Still referring to FIG. 2, it is seen that the cavity 22 is configured with holes 18a to receive a chemical indicator 24 and a biological indicator 26. In the preferred embodiment, a biological indicator of the type disclosed in presently pending U.S. application Ser. No. 579,924, which is assigned to the assignee of the present invention, is very suitable for use with the test pack 10 of the present invention. Further, a chemical indicator 24 of the type described and claimed in U.S. Pat. No. 2,118,144 is appropriate for use in the present invention.

In addition to base pad 20, test pack 10 also includes a top pad 28. Preferably, top pad 28 comprises a single porous sheet having an edge 46. Unlike base pad 20, top pad 28 is continuous and is not formed with a cavity. In the construction of test pack 10, top pad 28 is positioned against top surface 40 of base pad 20 with its edge 46 substantially flush with edge 44 of base pad 20. Also, top pad 28 is positioned against base pad 20 in such a way that the biological indicator 26 and the chemical indicator 24 can be held within the cavity 22. Further to this purpose, as also shown in FIG. 2, a bottom pad 30, which preferably comprises a plurality of porous sheets which are stacked to form the box-shaped pad 30 having an edge 48, is disposed against the bottom surface 42 of base pad 20 with its edge 48 substantially flush with edge 44 of base pad 20. Like the sheet 16 of top pad 28, the sheets 16 of bottom pad 30 are continuous and do not form a cavity. For the purpose of description, the box-shaped structures described herein are essentially the equivalent of right parallelepipeds.

An impermeable layer 32, which can be of any material which is nonporous and gas impermeable, is disposed against the top pad 28 in a manner well known in the pertinent art. Placement of layer 32 on top pad 28 in such a manner prevents the passage of gas transverse to the surface of top pad 28 where layer 32 is in contact with top pad 28. Stated differently, gas impermeable nonporous layer 32 is positioned against top pad 28 to direct the passage of gas into and out of the test pack 10 transverse to the exposed surface of bottom pad 30. In the preferred embodiment, the impermeable layer 32 comprises a plastic film which is laminated to top pad 28. Although layer 32 is shown laminated to top pad 28 in FIG. 2, it will be appreciated by the skilled artisan that impermeable layer 32 can be positioned against top pad 28 in any manner which will prevent flow of gas transverse to impermeable layer 32. Also, it will be appreciated by the skilled artisan that sheet 16 of top pad 28 essentially provides support for impermeable layer 32 and could be eliminated if an impermeable layer 32 of sufficient stiffness is used.

In accordance with the above description, in the preferred embodiment of the present invention, bottom pad 30 comprises approximately twenty-five undie cut sheets 16; base pad 20 comprises approximately forty die cut sheets 16; and top pad 28 comprises a single undie cut sheet 16. Further, the plastic gas impermeable layer 32 is preferably laminated across the entirety of the exposed outer surface of sheet 16 of top pad 28. Accordingly test pack 10 when stacked together will comprise from top to bottom; the plastic laminate gas impermeable layer 32, the gas permeable top pad 32 comprising a single undie cut sheet 16, the gas permeable base pad 20 comprising approximately forty die cut sheets 16 forming cavity 22, and the gas permeable bottom pad 30 comprising approximately twenty-five undie cut sheets 16.

Figure 4:
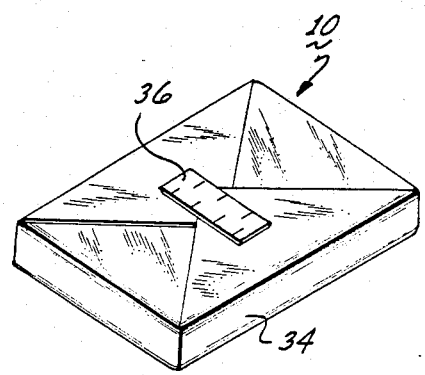
FIG. 4 is a perspective view of the sterilization test pack folded and ready for use in sterilization equipment.

The integrity of the entire test pack 10 can be maintained by folding a disposable CSR wrap around the test pack 10 and holding the CSR wrap in place with an autoclave tape 36. As best seen in FIG. 4, test pack 10, when constructed in the above described manner, comprises a self-contained unit which can be easily handled by personnel desiring to test the efficacy of sterilization equipment.

OPERATION

In the operation of the test pack 10 of the present invention, a biological indicator 26 and/or a chemical indicator 24 is placed within the cavity 22 that is formed within the porous base pad 20. A porous top pad 28 is positioned against the top surface 40 of middle pad 20 and a porous bottom pad 30 is positioned against the bottom surface 42 of middle pad 20 to confine the chemical indicator 24 or the biological indicator 26 within the cavity 22. An impermeable layer 32 is positioned against the top pad 28 in a manner which will confine the introduction of gas into and evacuation of gas from the test pack 10 to the edges 44, 46 and 48 and transverse to the exposed surface of bottom pad 30. The test pack 10 is then wrapped in disposable CSR wrap and held together by autoclave tape 36 in a manner which allows placement of the test pack 10 into a sterilization equipment 12 for testing of the equipment 12. After completion of the sterilization cycle, test pack 10 is removed from equipment 12 and the indicators 24 and 26 are examined to determine the efficacy of the cycle.

In an alternate embodiment of the present invention, generally designated 80 in FIG. 5, the preferred embodiment is altered to further comprise a layer 50 of reticulated foam which is positioned against the exposed surface of bottom pad 30 to position bottom pad 30 between base pad 20 and the foam layer 50. Additionally, a cover pad 52 is positioned to place foam layer 50 between bottom pad 30 and cover pad 52. A gas impermeable nonporous layer 38 is laminated against cover pad 52 in a manner similar to the description above for top pad 28 and impermeable layer 32.

In yet another embodiment of the present invention, as shown in FIG. 6, the top pad 28 is constructed solely of a gas impermeable nonporous layer 32. For the integrity of pack 10 and ease of construction, the impermeable layer 32 in this alternate embodiment should be of a plastic well known in the art which is sufficiently stiff to provide the support for chemical indicator 24 and/or biological indicator 26 as they nest in the cavity 22. In all important respects, the embodiment of the present invention, as shown in FIG. 6, is constructed in a manner as described for the preferred embodiment and functions essentially in the manner as described above for the preferred embodiment.

The skilled artisan will recognize that the present invention is capable of several variations and modifications. For instance, instead of a single sheet 16 for top pad 28, as disclosed for the preferred embodiment, top pad 28 may comprise a plurality of sheets 16 as shown in FIG. 5. An increase in the number of sheets 16 for top pad 28 will decrease the exposure of indicator 26 to radiant heat. Likewise the number of sheets 16 used for base pad 20 and bottom pad 30 can be varied according to the desires and needs of the operator. Further, although the preferred dimension of sheets 16 are 4.5"×6", these dimensions can also be changed to vary the resistance of test pack 10 and meet the particular needs and desires of the operator.

While the particular test pack as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A disposble pack for testing the efficacy of a sterilization process comprises:
    a plurality of gas permeable porous sheets, each of said sheets being cut to form a hole therethrough and stacked to form a base pad having a top surface, a bottom surface, an edge therebetween and a cavity established by the alignment of said holes for receiving a sterilization indicator therein;
    a top pad having an edge and disposed against said top surface with its edge substantially flush with said edge of said base pad;
    a porous bottom pad having an edge and disposed against said bottom surface with its edge substantially flush with said edge of said base pad; and
    a gas impermeable layer disposed against said top pad to substantially direct the passage of gas into and out of said pack through said edges of said top pad, said middle pad and said bottom pad and through said bottom pad.

2. A disposable pack as cited in claim 1 further comprising a gas permeable porous overwrap surrounding said pack to maintain the integrity thereof.

3. A disposable pack as cited in claim 2 wherein the sterilization indicator is a biological indicator.

4. A disposable pack as cited in claim 2 wherein the sterilization indicator is a chemical indicator.

5. A disposable pack as cited in claim 2 wherein the sterilization indictor comprises a biological indicator and a chemical indicator.

6. A disposable pack as cited in claim 2 wherein said top pad comprises a single gas permeable porous sheet and said bottom pad comprises a plurality of gas permeable porous sheets.

7. A disposable pack as cited in claim 2 wherein said gas impermeable layer is a plastic laminate.

8. A disposable biological test pack for testing the efficacy of a sterilization process comprises:
    a plurality of gas permeable porous sheets, each of said sheets being cut to form a hole therethrough and stacked to form a base pad having a top surface, a bottom surface, an edge therebetween and a cavity established by the alignment of said holes for receiving a sterilization indicator therein;
    a top pad having an edge and a gas impermeable layer laminated to said top pad to prevent the passage of gas into and out of said pack through said impermeable layer and positioned against said top surface of said base pad with its edge substantially flush with said edge of said base pad; and
    a porous bottom pad having an edge and disposed against said bottom surface with its edge substantially flush with said edge of said base pad.

9. A disposable pack as cited in claim 8 further comprising a gas permeable porous overwrap surrounding said pack to maintain the integrity thereof.

10. A disposable pack as cited in claim 9 wherein the sterilization indicator is a biological indicator.

11. A disposable pack as cited in claim 9 wherein the sterilization indicator is a chemical indicator.

12. A disposable pack as cited in claim 9 wherein the sterilization indicator comprises a biological indicator and a chemical indicator.

13. A disposable pack for testing the efficacy of a sterilization process comprises:
    a plurality of porous sheets, each having a hole cut therethrough and stacked to form a base pad having a top surface, a bottom surface, an edge therebetween and a cavity established by the alignment of said holes for recieving a sterilization indicator therein;
    a top pad having an edge and a surface disposed against said top surface with its edge substantially flush with said edge of said base pad;
    a porous bottom pad having an edge and disposed against said bottom surface with its edge substantially flush with said edge of said base pad;
    a gas impermeable nonporous layer disposed against said top pad to substantially direct the passage of gas into and out of said pack through said edge of said base pad and through said top pad;
    a layer of reticulated foam having an edge and disposed against said bottom pad with its edge flush with the edge of said bottom pad to position said bottom pad between said foam layer and said base pad; and
    a cover pad having an edge and a surface covered with a gas impermeable nonporous plastic laminate and disposed against said foam layer opposite said bottom pad with its edge substantially flush with the edge of said foam layer.

14. A disposable pack as cited in claim 13 further comprising a gas permeable porous overwrap surrounding said pack to maintain the integrity thereof.

15. A disposable biological test pack for testing the efficacy of a sterilization process comprises:
    a plurality of gas permeable porous sheets, each of said sheets being cut to form a hole therethrough and stacked to form a base pad having a top surface, a bottom surface, an edge therebetween and a cavity established by the alignment of said holes for receiving a sterilization indicator therein;

a porous bottom pad having an edge and disposed against said bottom surface with its edge substantially flush with said edge of said base pad; and a gas impermeable top pad having an edge and disposed against said top surface with its edge substantially flush with said edge of said pad to direct the passage of gas into and out of said pack through said edges of said middle pad and through said bottom pad.

16. A disposable pack as cited in claim 15 further comprising a gas permeable porous overwrap surrounding said pack to maintain the integrity thereof.

17. A disposable pack as cited in claim 16 wherein the sterilization indicator is a biological indicator.

18. A disposable pack as cited in claim 16 wherein the sterilization indicator is a chemical indicator.

19. A disposable pack as cited in claim 16 wherein the sterilization indicator comprises a biological indicator and a chemical indicator.

20. A disposable pack as cited in claim 16 wherein said top pad comprises a single gas impermeable layer and said bottom pad comprises a plurality of gas permeable porous sheets.

* * * * *